United States Patent [19]

Butte, Jr. et al.

[11] 4,222,961

[45] Sep. 16, 1980

[54] PROCESS FOR HYDROGENATING AROMATIC DINITRILES

[75] Inventors: Walter A. Butte, Jr., West Chester; William J. Murtaugh, Eddystone; Howard P. Angstadt, Media, all of Pa.

[73] Assignee: Suntech, Inc., Philadelphia, Pa.

[21] Appl. No.: 8,313

[22] Filed: Feb. 1, 1979

[51] Int. Cl.$^2$ ............................................. C07C 85/00
[52] U.S. Cl. ................................................ 260/563 D
[58] Field of Search .................................... 260/563 D

[56] References Cited

U.S. PATENT DOCUMENTS

| | | | |
|---|---|---|---|
| 2,606,925 | 8/1952 | Whitman | 260/563 D |
| 2,945,063 | 7/1960 | Quinn et al. | 260/563 D |
| 3,014,966 | 12/1961 | Freifelder et al. | 260/563 D |
| 3,117,992 | 1/1964 | Duggan | 260/563 D |
| 3,152,184 | 10/1964 | Levering | 260/563 D X |
| 3,177,258 | 4/1965 | Rylander et al. | 260/563 D X |
| 3,799,983 | 3/1974 | Corr et al. | 260/563 D |
| 4,049,584 | 9/1977 | Weissel | 260/563 D X |
| 4,070,399 | 1/1978 | Butte | 260/563 D |

*Primary Examiner*—Paul F. Shaver
*Attorney, Agent, or Firm*—J. Edward Hess; Donald R. Johnson; Paul Lipsitz

[57] ABSTRACT

A process for the hydrogenation of aromatic dinitriles to the corresponding cycloaliphatic aminomethyl compounds by (1) hydrogenating the nitrile in an ether solvent containing water and ammonia using nickel or cobalt as catalyst,
(2) removing by-products from the aromatic diamine thus produced,
(3) subjecting the aromatic diamine to hydrogenation with a ruthenium catalyst in an aqueous solvent system devoid of ammonia and
(4) isolating the cycloaliphatic diamine product.

5 Claims, 3 Drawing Figures

PROCESS FOR HYDROGENATING AROMATIC DINITRILES

CROSS REFERENCE TO RELATED APPLICATIONS

This application is related to the following applications filed of even date herewith:

Walter A. Butte, Jr. and Howard P. Angstadt entitled Hydrogenation of Aromatic Amines, Ser. No. 8,309.

Walter A. Butte, Jr., William J. Murtaugh and Richard E. Mitchell, entitled Hydrogenation of Aliphatic Nitriles to Primary Amines, Ser. No. 8,315.

Walter A. Butte, Jr. and William J. Murtaugh entitled Hydrogenation of Aromatic Nitriles to Primary Amines, Ser. No. 8,310.

This invention relates to a process for making cycloaliphatic aminomethyl compounds from aromatic nitriles, particularly those of the benzene and naphthalene series and enables high yields of amine product to be obtained efficiently and with prolonged catalyst life.

It is known in the art to effect hydrogenation of aliphatic and aromatic nitriles to the corresponding amines in the presence of various catalytic materials. It is also known to subject aromatic aminomethyl compounds to catalytic hydrogenation to convert them to the corresponding cycloaliphatic amine.

Hydrogenation of aliphatic and aromatic nitriles to the corresponding amines is accomplished in the presence of various catalytic materials. For example, U.S. Pat. No. 3,069,469 discloses the hydrogenation of aromatic nitriles with a combined cobalt and nickel catalyst where the nitrile, hydrogen, ammonia, and solvent (such as the isomeric xylenes, dioxane, and aliphatic alcohols) are brought into contact with the catalyst. A combined cobalt-nickel catalyst is employed in order to reduce the amount of undesirable secondary amines which contaminate the desired primary amine products and this phenomenon is common in nitrile hydrogenation. Another disclosure of interest is U.S. Pat. No. 3,252,248 which details the catalytic hydrogenation of organic nitrogen-containing carbon compounds (including aliphatic and aromatic nitriles) to amines in a liquid phase system using a specifically prepared sintered catalyst of cobalt or nickel. Because such specially prepared catalysts are said to be of high mechanical strength they are suitable when used in a method in which the initial material, either alone or in admixture with a solvent such as water, tetrahydrofuran, ammonia, methanol or the reacton product formed, is trickled together with hydrogen over the catalyst in a reaction tube. In Example 1 of this patent, an aliphatic nitrile (aminoacetonitrile) is hydrogenated in a mixture of liquid ammonia and an aqueous aminonitrile solution (about 8% of the liquid being water) in the presence of the specially prepared sintered catalyst to obtain ethylenediamine. In Example 11 where isophthalonitrile is the starting material a non-aqueous system is employed.

A process for hydrogenation of aromatic dinitriles to the corresponding diamines is also disclosed in United Kingdom Pat. No. 1,149,251. In this disclosure the dinitrile is hydrogenated with a zirconium promoted cobalt catalyst in the presence of ammonia using a solvent system such as aliphatic or aromatic hydrocarbons, aliphatic alcohols, dimethylformamide and dioxane. Example 3 of this disclosure illustrates hydrogenation of isophthalonitrile in a methanol-water mixture, but the amounts of the solvent components is not given.

Also of interest is the publication of H. Rupe and E. Hodel in Helv. Chem. Acta 6 865–880 (1923) which points out that in the hydrogenation of nitriles with a nickel catalyst in an aqueous system at atmospheric pressure, the water reacts with intermediates to form significant aldehydes which, in turn, leads to secondary amines being present in the reaction product.

A later publication (U.S. Pat. No. 3,372,195, 1968) confirms that water is detrimental in reducing nitriles to primary amines. In U.S. Pat. No. 3,372,195 it is reported that numerous types of nitriles including aliphatic and aromatic nitriles and cyanoethylated glycols may be converted to the corresponding primary amines by hydrogen reduction under pressure with a ruthenium catalyst in the presence of ammonia, using as a solvent system any one of a number of solvents including water. However, the disclosure adds that with nitriles having a molecular weight lower than about 200, water is not preferred due to its tendency to cause increased by-product formation.

There is also prior art of interest pertaining to the hydrogenation of aromatic aminomethyl compounds to the corresponding cycloaliphatic amines. Thus, for example, French Pat. No. 1,305,090 discloses that m-xylene-diamine may be hydrogenated to saturate the ring in a non-aqueous system using a supported ruthenium and/or rhodium catalyst. This reference also discloses the desirability of adding ammonia to the system if the maximum amount of primary amine is desired, it being known that the presence of ammonia suppresses the formation of secondary and tertiary amines which could be formed during the hydrogenation. In such hydrogenation processes the rates of reaction are frequently low and yields of product are not as high as desired. Also, because numerous by-products are formed during the reaction the catalyst becomes poisoned and cannot be repeatedly reused without a regeneration step.

The above referred to U.K. Pat. No. 1,149,251 also discloses that the aromatic diamine produced by hydrogenation of the dinitrile may be further hydrogenated to the cycloaliphatic diamine with or without isolation of the aromatic diamine using a ruthenium catalyst in a solvent system (saturated aliphatic hydrocarbons or ethers) in the presence or absence of ammonia.

It has now been found that aromatic dinitriles may be converted to the corresponding cycloaliphatic diamine in excellent yield and specificity by a novel four step procedure. In accord with the invention aromatic dinitriles, particularly of the benzene and naphthalene series, are converted to the corresponding cycloaliphatic aminomethyl compounds by (1) hydrogenating the nitrile in an ether solvent containing water and ammonia using nickel or cobalt as catalyst, (2) removing by-products from the aromatic diamine thus produced, (3) subjecting the purified aromatic diamine to hydrogenation with a ruthenium catalyst in an aqueous solvent system devoid of ammonia and (4) isolating the cycloaliphatic diamine product.

In carrying out the first step of the process of the invention an aromatic dinitrile, preferably of the benzene and naphthalene series, is catalytically hydrogenated with nickel or cobalt to a primary diamine in a solvent system comprising an ether, ammonia and an amount of water of from about 10% to about 20% by volume of the solvent used. It is the presence of the specific amount of water in this step that significantly contributes to the advantages of the process.

One particularly valuable improvement is the increase in reaction rate that is obtained together with high yields of aromatic amine product. Another advantage is that the formation of unwanted secondary amine by-products is suppressed. This is quite unexpected in view of the Rupe and Hodel teachings discussed above. Also, the use of water in the hydrogenated reaction of this invention enables the nickel or cobalt catalyst to be reused repeatedly without adverse effects.

In this first step of the process of the invention a mixture of the solvent, nitrile, ammonia, water and catalyst is heated to a reaction temperature of from about 85° C. to about 150° C., preferably about 115° C. and hydrogen introduced, with stirring, to a hydrogen pressure of from about 500 to about 3000 psig. The reaction is allowed to proceed until hydrogen uptake ceases or until aliquot samples show that all of the nitrile has been converted. Then, the reactor is cooled and vented and the contents are removed and filtered to recover the catalyst. The filtrate is distilled to recover solvent and the product is distilled under reduced pressure for use in the next step of the overall process.

This hydrogenation of dinitrile to diamine may be carried out with a wide variety of aromatic dinitriles, but will preferably employ those of the benzene or naphthalene series such as phthalonitrile, isophthalonitrile, terephthalonitrile, 1- or 2-cyanonaphthalene, 1,2-, 1,4-, 1,6, 2,6 or 1,8-dicyanonaphthalene and the like. It will be understood that the aromatic ring may have substituents such as lower alkyl (methyl, ethyl, butyl, etc.), halogen, alkoxy, and similar groups inert to the hydrogenation.

The solvent used will be an ether or a polyester (di- or tri-preferred) preferably with 4 to 6 carbon atoms and a carbon to oxygen ratio of from 2:1 to 5:1. Preferably cyclic ethers such as dioxane, tetrahydrofuran, ethylene glycol dimethyl ether and diethylene glycol dimethyl ether will be used. Cyclic ethers such as dioxane and tetrahydrofuran are most preferred.

The yield of primary diamines produced in the process declines as the concentration of nitrile in the solvent is increased. In general, satisfactory results are obtained with up to about 25% nitrile by weight based on solvent. Lower concentrations are preferred but practical considerations will normally dictate about 5% as the lower limit.

The catalyst used will be a conventional nickel or cobalt hydrogenation catalyst and may be a skeletal catalyst such as Raney nickel or Raney cobalt or the catalyst may be supported on a support such as alumina, silica, kieselguhr, silica-alumina and the like. Preferably, the supported catalyst will be prereduced with hydrogen and contains 75–95% nickel or cobalt and will have a silica and/or an alumina type binder. The amount of catalyst used is not critical, but will usually be from 1 to about 20 wt. percent of the nitrile in a batch hydrogenation process.

The process can also be carried out in a continuous trickle bed reactor. In that case, the nitrile solution and hydrogen are passed thru a catalyst bed and the catalyst is present in large excess over the nitrile contained in the reaction zone.

The amount of ammonia in the reaction mass will be from about 10% to about 30% by volume of the solvent. The ammonia is believed to be helpful in supressing the formation of unwanted secondary and tertiary amine by-products.

Figure 1:
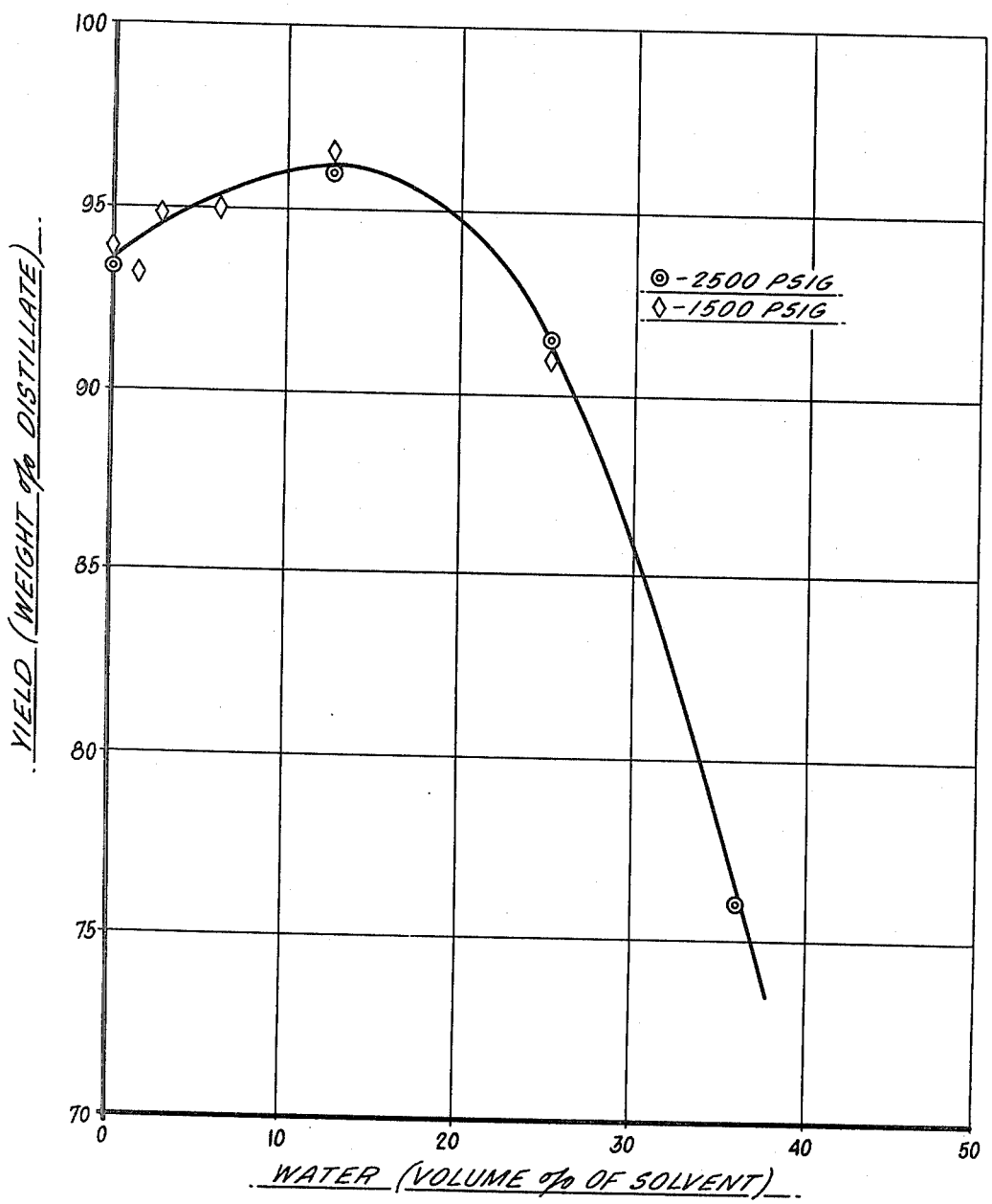
FIG. 1 is a graph showing how the yield of amine is affected by various amounts of water in the reaction mass of the first step of the process.
Figure 2:
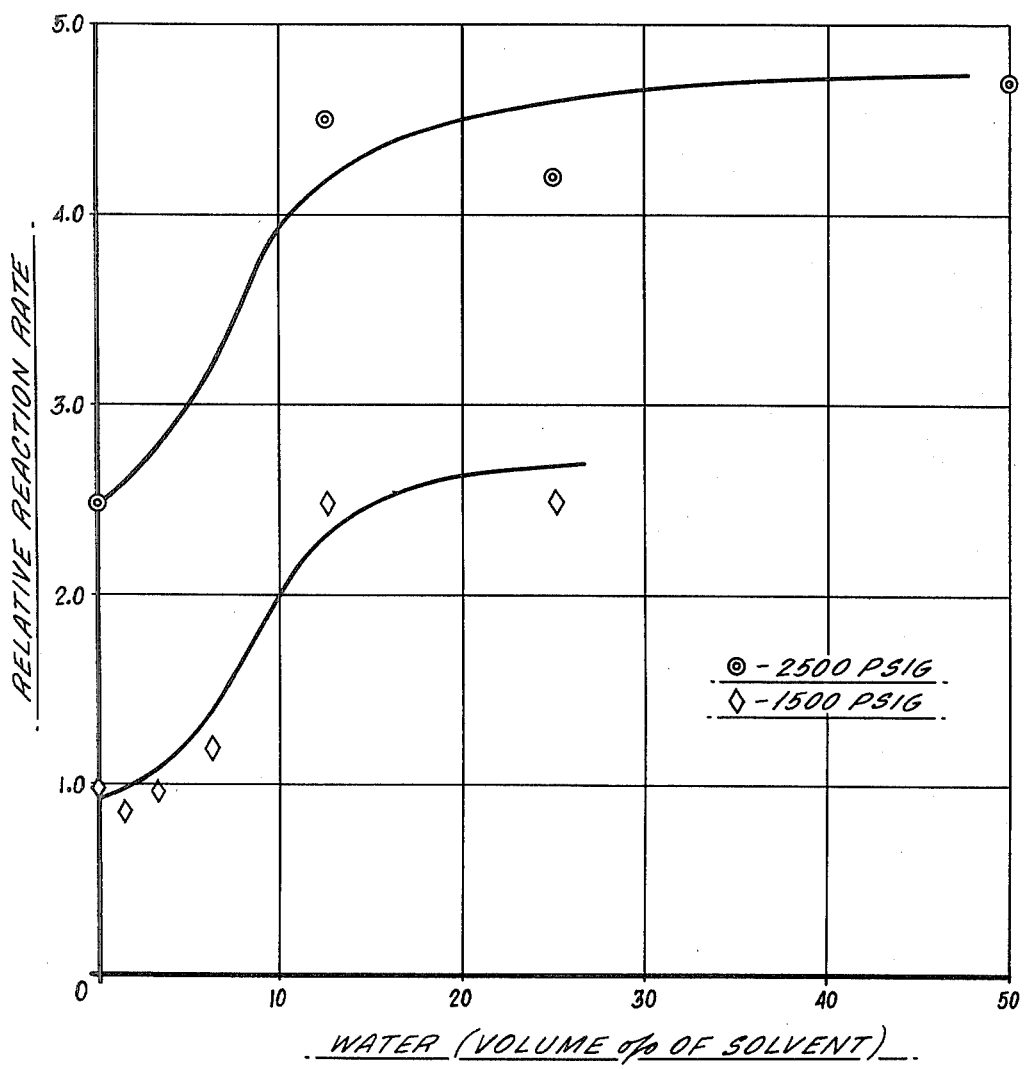
FIG. 2 shows the rate of reaction versus water concentration.
Figure 3:
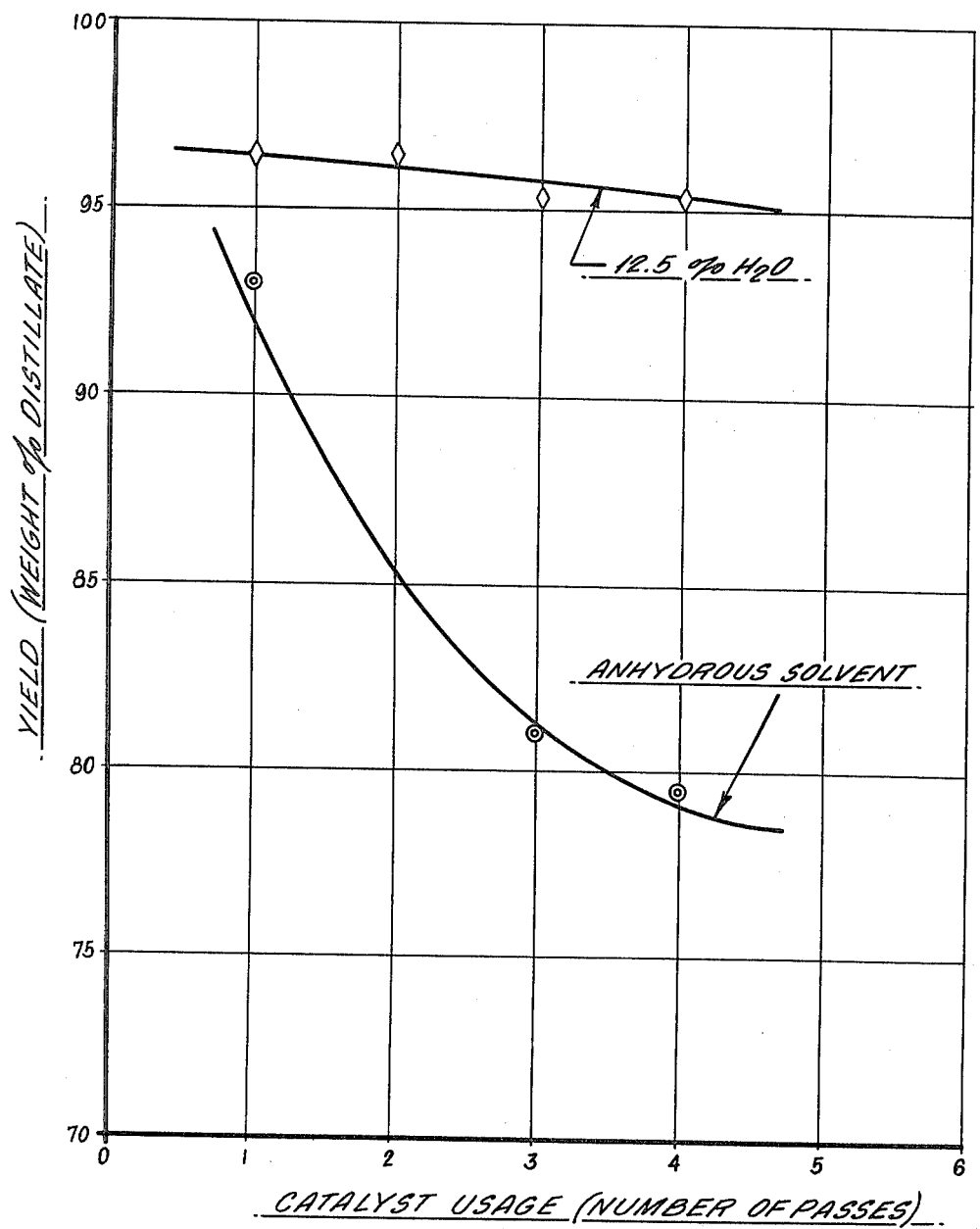
FIG. 3 shows how the catalyst may be recycled in the process of the invention.

The presence of a specific amount of water in the reaction mass is critical to the operation of the invention. In general, polymeric products result when hydrogenation of nitrile is carried out in an aqueous system containing ammonia. However, by controlling the amount of water to from about 10% to about 20% by volume of the solvent used, the product is the desired primary amine in high yield. This effect is shown in FIG. 1 where the preferred water range of from about 12% to about 15% is evident. A further advantage of the effect of the specific amount of water in the reaction mass is shown in FIG. 2 where it is seen that the reaction rate is significantly enhanced at a water concentration of about 10%. As seen from this figure, more than 20% of water gives a further slight increase in reaction rate, but the yield of desired product falls off as is evident from FIG. 1. A still further, unexpected advantage of the presence of water in the process is evident from FIG. 3 where the effect of water on catalyst recycling is seen. It is clear from this figure that in an anhydrous system, catalyst efficiency falls off quickly with repeated use of the catalyst. On the other hand, where 12.5% water is present, yields of product remain high when the catalyst is recycled.

In order to illustrate further the first step of the invention the following examples are given:

EXAMPLE 1

A stirred autoclave was charged with 400 ml. tetrahydrofuran (THF), 100 ml. ammonia, 50 g. terephthalonitrile (TPN) and 6.0 g. cobalt supported catalyst and various amounts of water. The autoclave was heated to 120° C. Hydrogen was introduced rapidly until the selected pressure was reached. The absorption of hydrogen started immediately and additional hydrogen was added to keep the pressure at the selected level. The course of the reaction was monitored by measuring the volume of hydrogen consumed and by periodic withdrawal of a small sample of the reaction mixture for analysis. When the analysis indicated that all of the terephthalonitrile had reacted, the agitation was stopped and the reactor was cooled rapidly and vented. The reaction mixture was filtered to recover the catalyst and then was flash evaporated to remove solvent. The residual oil was flash distilled at about 100° C. and 0.5 mm Hg. to give practically pure p-xylylene diamine. A small amount of high boiling residue remained in the distillation pot. Results of experiments conducted with various amounts of water and at 1500 and 2500 psig are listed in Table I.

The data in Table I and as plotted in FIG. 1, show that the addition of about 10% of water is beneficial in promoting a higher reaction rate and higher yield of primary amine (distillate). With quantities of water, beyond about 20%, the yield of distillate is reduced.

The data in Table IA further illustrates the first step of the process of the invention and illustrates the effective use of skeletal type catalysts. It will be noted that in the case of both Raney nickel and Raney cobalt both rate and selectivity to p-xylylene diamine (PXDA) is significantly increased when water is present. On the other hand, when a catalyst is used including a metal other than nickel or cobalt (e.g. nickel plus chromium) the benefits obtained by water addition are not significant; e.g. with nickel and chromium the rate decreased slightly and the increase in specificity was not significant.

EXAMPLE 2

Catalyst recovered from the experiment of Example 1 in which 12.5% water was used was recharged repeatedly to the autoclave in an otherwise identical procedure carried out at 1500 psig. Parallel experiments were also conducted without the addition of water. The results are summarized in Table II.

The data in Table II show that the yield of distillate product declines rapidly with catalyst reuse in the absence of water. However, with water present, the catalyst can be used repeatedly without substantial change in its performance.

TABLE I

INFLUENCE OF WATER ON RATE AND SELECTIVITY OF SUPPORTED COBALT CATALYST

Charge: 50 g. TPN, 100 ml. NH$_3$, 400 ml. THF; 3 g. (@ 2500 PSI) and 6 g (@ 1500 PSI) of Harshaw 1606 Cobalt Catalyst
Conditions: 115° C. @ 2500 PSI and 120° @ 1500 PSI

| Water %+ | Reaction time (min) | Rate* (hr.$^{-1}$) | Product Distillate wt. % |
|---|---|---|---|
| Pressure = 2500 psig | | | |
| 0 | 150 | 6.6 | 93.4 |
| 12.5 | 85 | 12 | 96.0 |
| 22 | 90 | 11 | 92.0 |
| 36 | 80 | 12 | 75.8 |
| Pressure = 1500 psig | | | |
| 0 | 190 | 2.6 | 94.0 |
| 1.5 | 225 | 2.2 | 93.2 |
| 3.1 | 195 | 2.6 | 94.8 |
| 6.3 | 160 | 3.1 | 95.0 |
| 12.6 | 75 | 6.6 | 96.4 |
| 23 | 80 | 6.2 | 91.0 |

+% by volume based on solvent
*wt. TPN reacted/wt. catalyst - hour

TABLE IA

INFLUENCE OF WATER ON RATE AND SELECTIVITY OF SKELETAL CATALYSTS

Charge: 50 g. TPN; 100 ml. NH$_3$; 400 ml. THF; 5.0 g. catalyst; 50 mls. H$_2$O as noted.
Conditions: 120° C., 1500 psi

| % H$_2$O | Rx Time (min.) | Rate (hr. $^{-1}$) | TPN Conv. % (%) | PXDA Selectivity (%) |
|---|---|---|---|---|
| Raney Nickel Catalyst (W.R. Grace #28): | | | | |
| 0 | 210 | 12.9 | 100 | 69.1 |
| 12.5 | 190 | 3.2 | 100 | 96.9 |
| Raney Cobalt Catalyst (W.R. Grace #27): | | | | |
| 0 | 230 | 2.4 | 94 | 40.3 |
| 12.5 | 187.4 | 3.1 | 98 | 89.2 |
| Raney Nickel-Chromium Promoted Catalyst (W.R. Grace #24): | | | | |
| 0 | 136.6 | 4.1 | 95 | 45.9 |
| 12.5 | 168 | 3.5 | 99 | 46.7 |

TABLE II

EFFECT OF WATER ON LIFE OF SUPPORTED COBALT CATALYST

| Pass No. | Reaction Time (min) | Relative Rate$^{(c)}$ | Product Yield (%) |
|---|---|---|---|
| No Water$^{(a)}$ | | | |
| 1 | 255 | 0.30 | 93.0 |
| 2 | 170 | 0.48 | n.a.* |
| 3 | 175 | 0.51 | 80.0 |
| 4 | 185 | 0.49 | 79.6 |
| 50 ml. water | | | |
| 1 | 75 | 1.00 | 96.4 |
| 2 | 90 | n.a.* | 96.4 |
| 3 | 110 | n.a.* | 95.4 |
| 4$^{(b)}$ | 105 | 0.91 | 95.4 |
| 5$^{(b)}$ | 100 | 1.00 | n.a.* |
| 6 | 110 | 1.01 | 93.2 |

$^{(a)}$Catalyst recovered from pass numbers one through four weighed 5.6, 5.1, 5.0 and 4.8 g. respectively.
$^{(b)}$Catalyst recovered from pass numbers three through five weighed 4.7, 4.4, and 4.0 g., respectively.
$^{(c)}$Adjusted for catalyst losses noted above.
*n.a. = not available

EXAMPLE 3

Table III illustrates the effect of various solvents in the reaction mass with and without water. As can be seen, water improves the reaction rate with THF, dioxane and xylene, but in the case of xylene the yield of product is very low (54.2%). Furthermore, the addition of water has a deleterious effect in the case of ethanol solvent. Thus, the unexpected specificity of the process is evident.

As indicated above, the second step of the process requires the removal of by-products formed in the first step producing the aromatic diamine. This is readily done by a simple distillation of the amine from the reaction mass, generally under vacuum conditions with temperature parameters determined by the boiling points of the particular amine. Thus, for example when hydrogenating terephthalonitrile, the reaction product from the first step is distilled under reduced pressure (around 1-5 mmHg.) using a slightly warm condenser to prevent the purified product, which melts at about 60°-65° C., from solidifying in the condenser. After first removing a small forecut, a white crystalline solid is obtained which is highly pure (99.6%) p-xylylene diamine and a small amount of dark residue remains in the distillation flask.

The distilled aromatic diamine is then subjected to the third step of the process which comprises hydrogenation of the aromatic bis-amine with a ruthenium catalyst in an aqueous solvent system devoid of ammonia.

Reaction conditions will be at a temperature of from about 50° to about 150° C. and at a pressure of between about 500 and about 2000 psig. These conditions are relatively mild and thereby provide another important advantage for the process since lower operating costs result from the use of mild conditions. It is also particularly surprising that hydrogenation of the aromatic ring can be made to occur under these relatively mild conditions. Preferred temperature for the process will be about 75° to about 130° C., and preferred pressure is from about 1000 to about 1500 psig. The catalyst, as indicated, will be supported ruthenium.

TABLE III

EFFECT OF WATER AND VARIOUS SOLVENTS ON RATE AND SELECTIVITY

Charge: 50 g. TPN, 6 g. Co catalyst, 100 ml. NH$_3$, 400 ml. diluent
Conditions: 120° C. 1500 psi

| Solvent | Water, % | Time (min.) | Rate (hr$^{-1}$) | Product Yield Wt. % |
|---|---|---|---|---|
| Ethanol | 0 | 150 | 3.3 | 87.4 |
| Ethanol | 12.5 | 155 | 3.2 | 72.0 |
| Xylene | 0 | 225 | 2.2 | — |
| Xylene | 12.5 | 85 | 5.8 | 54.2 |
| Dioxane | 0 | 140 | 3.6 | 94.6 |
| Dioxane | 12.5 | 90 | 5.6 | 94.0 |
| THF | 0 | 190 | 2.6 | 94.0 |
| THF | 12.5 | 75 | 6.7 | 96.4 |

Preferably, the useful supports will include carbon, alumina and activated alumina, silica, including synthetic gel and kieselguhr, calcium carbonate, titanium dioxide, bentonite, barium sulfate, etc. Preferably, the ruthenium catalyst (employed in the form of its black) will be from about 0.1 to 10 percent by weight of the total catalyst and support. These catalysts and their method of preparation are known in the art (see for example U.S. Pat. No. 3,117,162).

It is known in the art that catalysts often become inactive after prolonged use and this phenomenon may also occur with the catalyst used in this step of the invention. However, it has been found that the catalytic activity is readily restored by simply washing it with an aqueous mineral acid, preferably HCl and then rinsing the treated catalyst with water to remove all traces of residual acid.

In carrying out this ring hydrogenation step of the process the aromatic bis(aminomethyl) compound, water and catalyst are charged to the appropriate pressure reactor and after closing the reactor it is heated to a temperature of from about 50° C. to about 150° C. At this point hydrogen is pressured in the reactor to the desired pressure and, as stirring or other agitation is maintained, the uptake of hydrogen is observed. After hydrogen absorption stops, stirring is continued for a short time, the reactor cooled, opened and the contents filtered. The filtrate is distilled to separate the water solvent from the product. Isolation and purification of the product is readily accomplished by vacuum distillation.

It will be understood, of course, that in addition to carrying out the process by the batch technique described above, a continuous operation may also be used. In such a case, a packed bed of catalyst may be used through which the reaction solution and hydrogen are simultaneously passed.

The amount of water used in the reaction may vary over a wide range; about 1 part by weight of amine to about 1 to 10 parts of water will be used.

As indicated above, significant parameters for this step are the use of water as a solvent medium and the absence of ammonia from the system.

While it is not known with certainty why a water solvent gives the improved process it is speculated that the relatively high solubility of the aromatic diamine is at least partly responsible. For example, the solubility of p-xylene diamine in water is >150 g/100 g. H$_2$O, which is also unusual for an organic material and this polarity of the water is influential in keeping the catalyst surface washed free of impurities and/or generated catalyst poisons, thus resulting in longer catalyst life.

Also it would be expected, in view of the prior art teaching to add ammonia during nitrile reductions to retard formation of secondary and tertiary amines, that it would be desirable to use ammonia in the reaction system. However, it is found that with the system of the invention, ammonia is detrimental and should not be used. The solvent system is preferably essentially entirely aqueous, but other conventional ether-type solvents such as tetrahydrofuran, the dimethylether of ethylene glycol (e.g. DIGLYME), and the like may be present generally in amounts less than about 50% by weight of the water used.

In order to illustrate further the invention the following examples are given:

EXAMPLE 4

Five hundred grams of crude solid para-xylyene diamine (PXDA) was dissolved in 500 g. of distilled water and 2 g. of 5% ruthenium catalyst supported on alumina added. The solution was then charged to a two liter autoclave and heated to 130° C. and then pressured to 1600 psi total pressure with hydrogen. As the reaction proceeded hydrogen was continually added so that the total pressure was maintained between 1500 and 1600 psi, recording the length of time required for each 100 psi drop in pressure. After over 900 minutes the rate of uptake was about ⅓ its original value and steadily decreasing. During this reaction the average time required to consume 100 psi of hydrogen was 23.6 min. Chromatographic analysis indicated that the diamine was 73% converted and the yield of 1,4-bis(aminomethyl)-cyclohexane (BAMCH) was 62% based on feed.

When this experiment was repeated using pure white solid diamine which had been distilled prior to use, 100% conversion of the diamine was obtained, the average time for consumption of 100 psi of hydrogen was 15.5 minutes and chromatographic analysis of the product indicated a yield of 1,4-bis(aminomethyl)cyclohexane of 88% based on charge.

This data demonstrates the importance on the rate of reaction and yield of desired product of using a pure starting material. Thus, when the aromatic bis(aminomethyl) compound is obtained by hydrogenation of the aromatic dinitrile it is important for optimum yield to purify the aromatic (bis(aminomethyl) compound before hydrogenation in accord with the process of this invention.

EXAMPLE 5

It has been generally accepted that carrying out hydrogenation to product amines is best done in an ammonia environment, but the following data in Table IV shows that in the reduction of xylylene diamines to bis(aminomethyl)cyclohexanes, water devoid of ammonia is a superior solvent to aqueous ammonia.

Table IV summarizes the results obtained from hydrogenating successive batches of 40 g. of para-xylylene diamine (PXDA) in 360 mls. of either aqueous ammonia or water using 2.0 g. 5% Ru/Al$_2$O$_3$ at 100° C. and hydrogen to make 1500 psig total pressure. The table lists the time required to take up cumulatively 600 psi of hydrogen. It can be readily seen that after 3 batches using NH$_3$/H$_2$O the temperature had to be raised to restore the rate of reaction (never returned to original rate) and during the 6th batch the catalyst became ineffective. Using water however, six batches were reduced before the temperature had to be raised.

by washing the catalyst with aqueous HCl and by using a purified PXDA starting reactant.

TABLE V

PXDA REDUCTION WITH 5% Ru/Al$_2$O$_3$
500 g. PXDA/500g. H$_2$O - 2 g. CATALYST

| Run | PXDA Reacted (g.) | % Conversion | BAMCH Formed (g.) | % Selectivity | Temp. °C. | Pressure (psig) |
|---|---|---|---|---|---|---|
| A | 325 | 65 | 304 | 93 | 100/125 | 1500/1400 |
| B | 153 | 31 | 142 | 93 | 125 | " |
| Note 1 | | | | | | |
| C | 498 | 99 | 347 | 70 | 125 | " |
| D | 458 | 92 | 404 | 88 | 125 | " |
| E | 364 | 73 | 311 | 85 | 130 | 1600/1500 |
| Note 2 | | | | | | |
| F | 500 | 100 | 440 | 88 | 130 | " |
| G | 486 | 97 | 453 | 93 | 130 | " |
| H | 486 | 97 | 381 | | | |

Note 1 Washed catalyst with 4N HCl after run B and after each subsequent experiment.
Note 2 Used purified (distilled) PXDA for all subsequent experiments.

On raising the temperature the original rate of reaction was obtained and the catalyst remained active after ten such reductions. This data illustrates the beneficial effect of using water for this reduction.

TABLE IV

HYDROGENATION OF PXDA IN AMMONIA-WATER AND WATER
(360 mls solvent; 40 g. PXDA 2 g. 5% Ru/Al$_2$O$_3$, 100° C. 1500 psig total

| Batch No. | NH$_3$/H$_2$O | | | | | | H$_2$O | | | | | | | | | |
|---|---|---|---|---|---|---|---|---|---|---|---|---|---|---|---|---|
| | 1 | 2 | 3 | 4# | 5# | 6# | 1 | 2 | 3 | 4 | 5 | 6 | 7# | 8# | 9# | 10 |
| Cummulative H$_2$ Uptake (psi) | Time (minutes) | | | | | | | | | | | | | | | |
| 100 | 10 | 10 | 46 | 23 | 32 | 70 | 12 | 16 | 25 | 29 | 12 | 33 | 11 | 5 | 6 | 10 |
| 200 | 18 | 32 | 75 | 40 | 62 | 160 | 22 | 34 | 50 | 54 | 36 | 72 | 23 | 21 | 21 | 30 |
| 300 | 25 | 50 | 101 | 59 | 83 | 195 | 32 | 54 | 77 | 79 | 62 | 107 | 34 | 35 | 36 | 40 |
| 400 | 35 | 70 | 135 | 74 | 115 | — | 45 | 75 | 102 | 107 | 90 | 136 | 45 | 46 | 50 | 54 |
| 500 | 47 | 89 | 159 | 92 | 151 | — | 66 | 98 | 132 | 136 | 118 | 179 | 58 | 57 | 61 | 65 |
| 600 | 75 | 108 | 196 | 112 | 203 | — | 96 | 125 | 173 | 168 | 151 | 220 | 72 | 72 | 79 | 79 |

Temperature raised to 125° C.

EXAMPLE 6

This example illustrates the reactivation of the catalyst after it loses some or all of its activity due to prolonged use.

A two-liter stainless steel autocalve was charged with 500 g. of PXDA, 500 g. water and 2. g. of 5% Ru/Al$_2$O$_3$, brought to 125° C. and charged to 1500 psig with hydrogen. Agitation was begun and the rate of hydrogen uptake was measured keeping the total pressure between 1400 and 1500 psig. The initial rate of conversion of the aromatic diamine to BAMCH at this temperature was 25.4 g./g-cat./hr. When the reaction was completed, the contents of the reactor were filtered and the catalyst reused with a second batch of amine under the same conditions of reaction. In this case the rate of conversion of the p-xylylene diamine fell to 12.6 g./g-cat./hr. Again the reactor was drained; this time the catalyst was slurried in a solution of 80 cc conc. HCl and 320 cc H$_2$O, filtered and extensively washed with water to remove all traces of acid. When this catalyst was reused with a fresh batch of diamine under identical reaction conditions the observed rate of PXDA conversion had returned to 26.4 g/g.-cat./hr.

EXAMPLE 7

Table V illustrates the results obtained in the hydrogenation of p-xylylenediamine (PXDA) with a catalyst of 5% ruthenium on alumina under various conditions. It will be seen that conversion is increased and high selectivity for desired product (BAMCH) is maintained Isolation of the product cycloaliphatic diamine is readily accomplished, preferably by disillation under reduced pressure. For example, in the case of preparing BAMCH, distillation at about 30 mm Hg yields a small forecut of light ends which is removed and pure BAMCH is obtained at about 138°-142° C. head temperature. The exact temperature for the pure product depends, of course, on the pressure and normal distillation parameters required for pure, colorless, liquid product.

Thus, in accord with the invention an aromatic dinitrile is readily converted to a cycloaliphatic diamine by a series of easily conducted process steps giving the final product in high yield, selectivity and purity. These cycloaliphatic diamines are of particular utility as polymer intermediates for polymeric fibers as intermediates for polyisocyanates which are useful for polyurethane foam, coatings fabrication, and bonding agents.

The invention claimed is:

1. A process for the hydrogenation of aromatic dinitriles to the corresponding cycloaliphatic aminomethyl compounds which comprises:

(1) hydrogenating the nitrile at a temperature of from about 85° to about 150° C. and at a pressure of from about 500 to about 3000 psig in ether solvent containing water and ammonia using nickel or cobalt as catalyst, the amount of water being from about 10% to about 20% by volume of the ether solvent and the amount of ammonia being from about 10% to about 30% by volume of ether solvent, (2) removing by-products from the aromatic diamine thus produced, (3) subjecting the purified diamine to hydrogenation at a temperature of from about 50° to about 150° C.

and at a pressure of from about 500 to about 2000 psig with a ruthenium catalyst in an aqueous solvent system devoid of ammonia and (4) isolating the cycloaliphatic aminomethyl product.

2. The process of claim 1 where the aromatic dinitrile is a member of the benzene and naphthalene series.

3. A process for the hydrogenation of aromatic dinitriles of the benzene series to the corresponding cycloaliphatic aminomethyl compound which comprises:

(1) hydrogenating the nitrile at a temperature of from about 85° to about 150° C. and at a pressure of from about 500 to about 3000 psig in a cyclic ether solvent containing water and ammonia using nickel or cobalt as catalyst, the amount of water being from about 11% to about 14% by volume of the ether solvent and the amount of ammonia being from about 10% to about 30% by volume of the ether solvent, (2) removing by-products from the aromatic diamine thus produced, (3) subjecting the purified diamine to hydrogenation at a temperature of from about 75° to about 130° C. and at a pressure of from about 1000 to about 1500 psig with a ruthenium catalyst in an aqueous solvent system devoid of ammonia and (4) isolating the cycloaliphatic aminomethyl product.

4. The process of claim 3 where the starting compound is terephthalonitrile.

5. The process of claim 3 wherein the catalyst activity is restored by washing said ruthenium catalyst with an aqueous mineral acid and washing the treated catalyst with water to remove residual acid.

* * * * *